United States Patent [19]

Ham et al.

[11] Patent Number: 5,267,151
[45] Date of Patent: Nov. 30, 1993

[54] METHOD AND APPARATUS FOR DETECTING AND IDENTIFYING A CONDITION

[76] Inventors: Frederic M. Ham, 460 Watson Dr.; Glenn M. Cohen, 146 Tampa Ave.; Samuel P. Kozaitis, 2260 Mockingbird La., all of, Indialantic, Fla. 32903

[21] Appl. No.: 578,793

[22] Filed: Sep. 7, 1990

[51] Int. Cl.$^5$ .................... G06F 15/00; G06F 15/18
[52] U.S. Cl. ................... 364/413.09; 395/22
[58] Field of Search .......... 364/413.09; 128/633, 128/677; 356/434; 395/22, 23

[56] References Cited

U.S. PATENT DOCUMENTS

| | | | |
|---|---|---|---|
| 4,655,225 | 4/1987 | Dähne et al. | 128/633 |
| 4,914,603 | 4/1990 | Wood | 364/513 |
| 5,146,541 | 9/1992 | Speidel | 395/21 |

Primary Examiner—Roy N. Envall, Jr.
Assistant Examiner—Khai Tran
Attorney, Agent, or Firm—Evenson, McKeown, Edwards & Lenahan

[57] ABSTRACT

A method and apparatus for sensing and classifying a condition of interest in a system from background noise in which a parameter representative of the condition of interest is sensed and an electrical signal representative of the sensed parameter is produced. The electrical signal is converted into a digital signal, this digital signal containing a signal of interest representative of the condition of interest and background noise. The digital signal is received by an artificial neural network which filters out the background noise to produce a filtered signal from the digital signal, and classifies the signal of interest from the filtered signal to produce an output representative of the classified signal.

25 Claims, 4 Drawing Sheets

METHOD AND APPARATUS FOR DETECTING AND IDENTIFYING A CONDITION

FIELD OF THE INVENTION

The present invention relates to the recognition and detection of a condition of a system, and more particularly, to a method and apparatus for detecting a signal of interest from a signal that contains a large amount of noise relative to a desired signal that is indicative of the condition to be detected. This is particularly useful in the field of biological sensing, such as the determination of glucose levels in blood.

BACKGROUND OF THE INVENTION

Glucose provides a substantial portion of the human body's energy needs. Because of its importance, the body continuously monitors glucose concentrations and maintains an optimal concentration through a complex interplay of hormones. Insulin dependent diabetes (Type I) occurs as a result of the body's inability to synthesize proper amounts of insulin. This results in carbohydrate protein and lipid catabolism. Insulin replacement is absolutely essential in this form of diabetes. Non-insulin dependent diabetes (Type II) occurs as a result of relative insulin deficiency. Both types of diabetes result in the chronic complications of retinopathy, nephropathy, coronary heart disease, stroke and pheripheral vascular disease.

Treatment of Type I diabetes involves diet, exercise, and insulin replacement in order to minimize the complications of the disease. The amount of insulin replacement is usually determined by periodically monitoring blood glucose levels using commercially available monitoring kits, involving the pricking of fingers, etc. However, even if insulin, diet, and exercise are properly maintained, complications can still result, since monitoring of glucose is not continuous. These sampling gaps emphasize the need for improved monitoring and the development of biosensors for monitoring glucose levels, with the potential for implantation. One type of biosensor is a chemical sensor that uses enzyme molecules which are immobilized in a permeable matrix for real-time measurements over a dynamic range of 0.1 to 20 mmol. Although accurate, chemical sensors share the common problem of requiring relatively frequent replenishment of the enzyme (e.g. every 30 days). Providing such a chemical sensor in vivo presents the obvious problem of frequent surgeries to implant and remove the chemical sensors.

Another problem with chemical sensors is that these sensors will lose their effectiveness, if implanted, when cells grow over the enzymatically impregnated membranes. There is therefore a need for a highly reliable and long-term in vivo non-chemical sensor that will detect glucose concentrations.

Recently, non-chemical sensors that are optical in nature have been proposed. These sensors would avoid the problems of chemical sensors, yet pose problems of their own. An optical sensor for detecting glucose is described in *Blood Glucose Measurement By Multiple Attenuated Total Reflection and Infrared Absorption Spectroscopy*, by Mendelson, et al., IEEE Transactions on Biomedical Engineering, Vol. 37, No. 5, May 1990. An optical analyzer that uses absorption spectroscopy in the infrared region as described in the above article avoids the need for replenishing enzymes and would also avoid the problem of cell growth over enzymatic membranes.

"Absorption spectroscopy" in the infrared region is a technique based upon the phenomena that each molecule of a biological substance has specific resonance absorption peaks which are known as "fingerprints". These unique characteristic peaks are caused by vibrational and rotational oscillations of the molecules. Biological molecules have very complex structures, and therefore possess a large number of absorption peaks in the infrared region. Many of the absorption peaks occur that overlap those of other molecules that exist in whole blood, such as cholesterol.

There are three basic problems associated with the detection of any biological substance in an aqueous solution using infrared absorption spectroscopy. These problems are: the intrinsic high background absorption of water; the large number of overlapping infrared absorption peaks of other molecules; and the degradation of the signal of interest due to noise that is usually caused by the instrument itself and interference due to other molecules.

Although the device proposed by Mendelson, et al. was able to detect a glucose IR signal in blood, despite the problem of overlapping absorbances, this device has to use high (non-physiological) glucose concentrations and a high energy $CO_2$ laser source.

There is therefore a need for a method and apparatus that will sense a particular condition (such as the glucose concentration in blood) and distinguish a signal of interest representative of that condition from background noise in the system and in the measurement device. If used as a glucose detector, for example, the method and device needs to be able to detect physiological glucose levels in blood with a low-energy selective source and a robust artificial neural network detection method.

SUMMARY OF THE INVENTION

The above and other needs are met by the present invention which provides a method of filtering and classifying a signal of interest from background noise, this method comprising the steps of receiving in an artificial neural network a digital signal containing a signal of interest and background noise, filtering out the background noise to produce a filtered signal from the digital signal in a feedforward perceptron of the artificial neural network, and classifying the signal of interest from the filtered signal in a counterpropagation network of the artificial neural network.

In another embodiment of the present invention a method of sensing and classifying a condition of interest in a system from background noise is provided. This method comprises the steps of sensing a parameter representative of the condition of interest and producing an electrical signal representative of the sensed parameter, converting the electrical signal into a digital signal, said digital signal containing a signal of interest representative of the condition of interest and background noise, receiving in an artificial neural network the digital signal containing the signal of interest and the background noise, filtering out the background noise in the artificial neural network to produce a filtered signal from the digital signal, and classifying the signal of interest from the filtered signal in the artificial neural network to produce an output representative of the classified signal.

Another embodiment of the present invention provides a device for filtering and classifying a signal of interest from background noise. This embodiment comprises means for receiving in an artificial neural network a digital signal containing a signal of interest and background noise, means for filtering out the background noise from the digital signal to produce a filtered signal, and means for classifying the signal of interest from the filtered signal.

Another embodiment of the present invention provides a device for sensing and classifying a condition of interest in a system from background noise. This embodiment comprises means for sensing a parameter representative of the condition of interest and producing an electrical signal representative of the sensed parameter, means for converting the electrical signal into a digital signal, this digital signal containing a signal of interest representative of the condition of interest and background noise, means for receiving in an artificial neural network the digital signal containing the signal of interest and the background noise, means for filtering out the background noise in the artificial neural network to produce a filtered signal from the digital signal, and means for classifying the signal of interest from the filtered signal in the artificial neural network to produce an output representative of the classified signal.

Another embodiment of the present invention provides a device for measuring a condition of a biological system. This embodiment comprises a sensor that senses a parameter representative of the condition of interest in the biological system, this sensor producing a signal representative of the sensed parameter and containing background noise, a converter coupled to the sensor to convert the signal produced by the sensor to a digital signal, this digital signal containing a signal of interest and background noise, and an artificial neural network coupled to the converter, this artificial neural network filtering the background noise from the digital signal to produce a filtered signal and classifying the signal of interest from the filtered signal in the artificial neural network to produce an output representative of the classified signal.

The embodiments of the present invention described above use an artificial neural network that is very robust since it both filters out background noise efficiently and also is performance invariant relative to threshold decision settings. The artificial neural network, in certain embodiments, is a hybrid network that includes a feed-forward perceptron for the filtering and a counter-propagation network for the classifying.

The use of an artificial neural network with a sensor that is based on infrared absorption and evanescent field spectroscopy allows for an in vivo implantation of the device for measuring, for example, the concentration of glucose levels in blood. The robustness of the artificial neural network is particularly advantageous because of the background noise caused by the presence of water and other biological molecules that have overlapping absorption spectra. This allows a particular range of the glucose spectrum to be used that is rich in spectral absorption peaks to provide a distinctive fingerprint of the substance to be detected. The use of this spectrum, allowed by the detection method of the present invention, gives rise to a higher probability of detection, as opposed to the single peak detection method described by Mendelson et al.

Other objects, advantages and novel features of the present invention will become apparent from the following detailed description of the invention when considered in conjunction with the accompanying drawings.

DETAILED DESCRIPTION OF THE DRAWINGS

Figure 1:
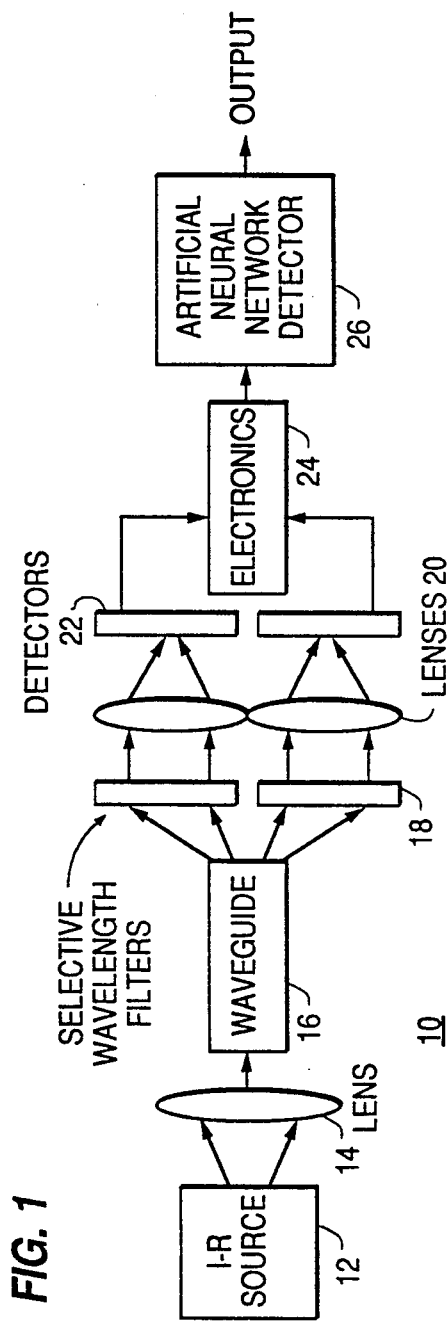
FIG. 1 is a schematic diagram of the apparatus of the present invention.

The sensing and detecting apparatus of the present invention 10 is illustrated in a block diagram form in FIG. 1. The sensor and detector 10 includes an infrared source 12 that is a non-chemical optical device. Accordingly, this IR source 12 can be used as the energy source for the in vivo sensor, and does not use enzymes that need to be replenished nor does it have an enzymatic cell membrane that will be covered over by cell growth. The sensing component of the sensor and detector 10 uses infrared absorption and evanescent field spectroscopy.

The infrared signal from the IR source 12 is provided through a lens 14 to a waveguide 16 that is, for example, a cladding-free infrared optical fiber available in the $2-11\mu$ region. Evanescent field spectroscopy (EFS) is an extension of the well-known technique of internal reflection spectroscopy. EFS has been utilized in sensing devices, using cladding-free multi-mode optical fibers for the detection of in situ concentrations of gases and liquids.

The waveguide 16 provides the absorbed infrared signal to selective wavelength filters 18. The output of the wavelength filters 18 are inputs to lenses 20 that focus the infrared signals on infrared detectors 22. One lens filters a portion of the infrared spectrum ($8.3\mu$ to $10.3\mu$) that is utilized for detection purposes. In this spectral region, for example, glucose has five relatively large absorption peaks. The other lens reflects a specific non-absorbing wavelength of glucose in the above spectral region. The spectral samples in this $8.3\mu$ to $10.3\mu$ range are normalized with respect to the non-absorbing peak for glucose in order to eliminate effects due to characteristics of the optical fiber.

Analog output signals are provided by the detectors 22 to an electronics circuit 24 that converts the analog signals from the detectors 22 to digital signals suitable for use by an artificial neural network detector 26. The electronics also performs differencing of the IR spectral content for water from the IR spectral content for glucose and the background noise.

The output of the artificial neural network detector 26 can be provided to, for example, an insulin pump (with the proper controller electronics) or a recording apparatus. The artificial neural network detector can be implemented using known VLSI techniques.

Figure 2:
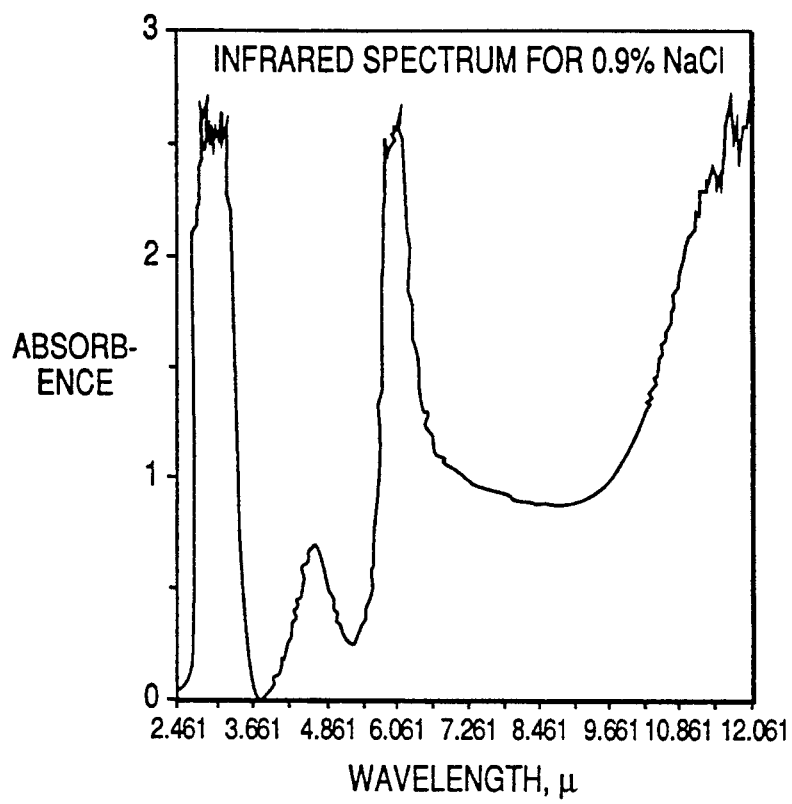
FIG. 2 is a graph of an infrared absorption spectrum for 0.9% NaCl solution.
Figure 3:
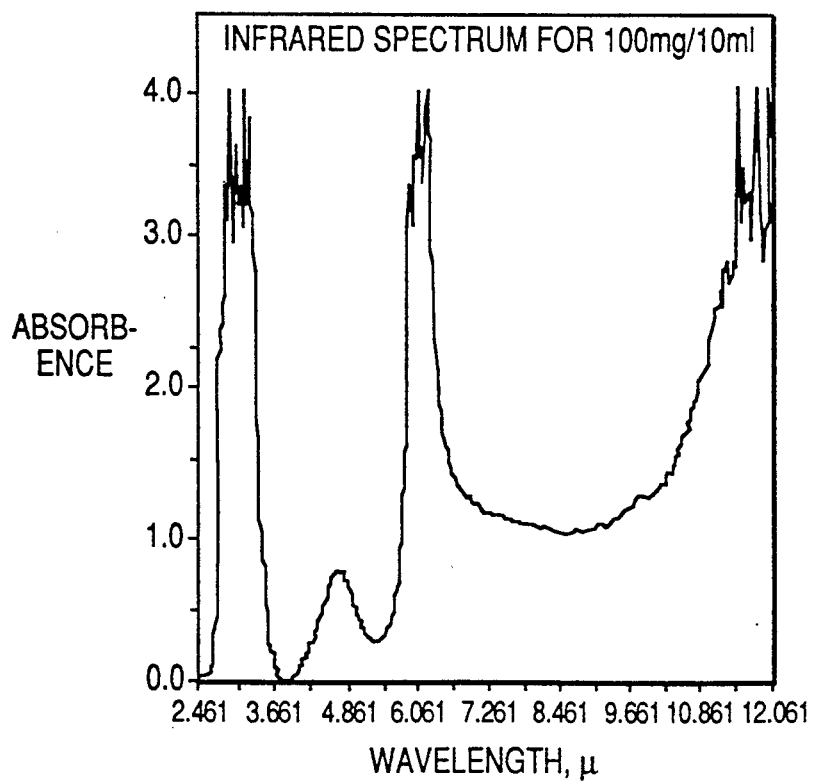
FIG. 3 is a graph of the infrared absorption spectrum for a 100 mg glucose/10 ml saline.
Figure 4:
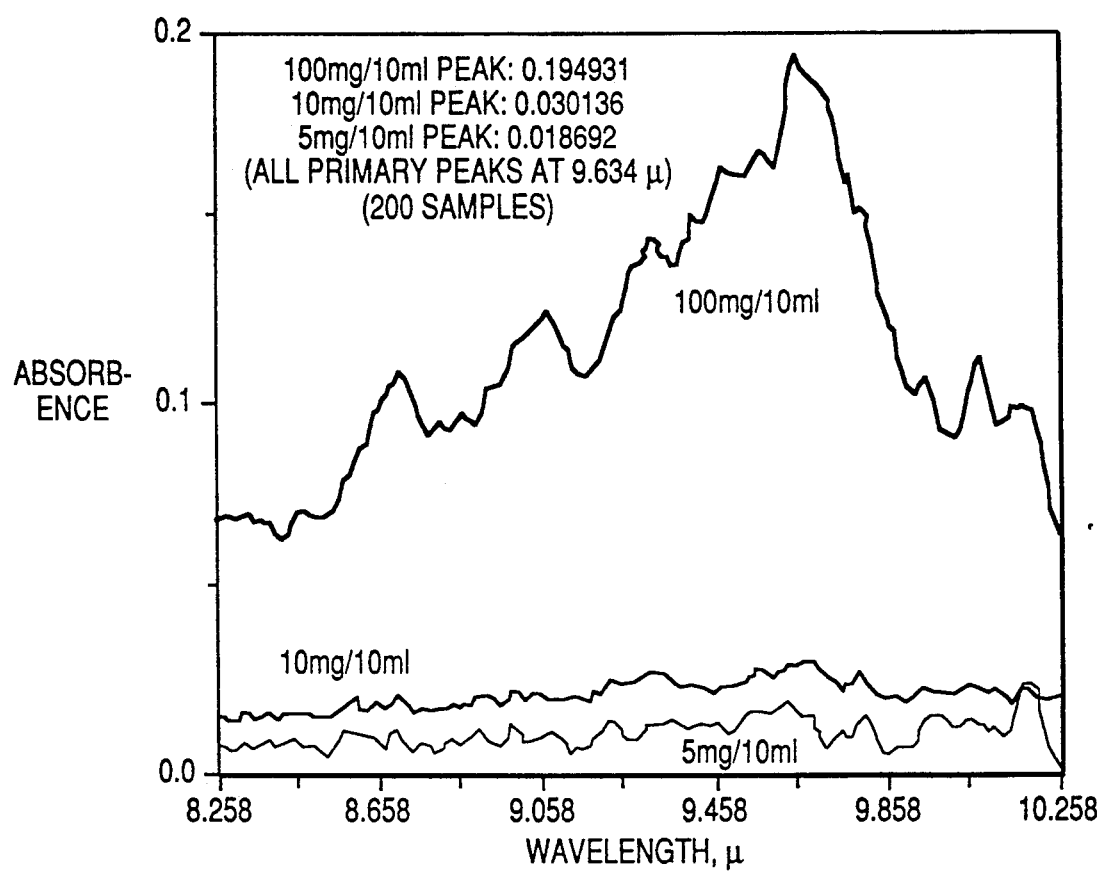
FIG. 4 is a graph of the infrared absorption spectrum for three concentrations of glucose and saline after subtraction of the pure 0.9% NaCl IR spectral data.

The high background absorption of water can be minimized by differencing the IR spectral data for the glucose in an aqueous solution with the spectral data for the pure saline solution. FIG. 2 shows the IR spectrum for 0.9% NaCl (saline) solution. In FIG. 3, the IR spectrum for 100 mg of glucose and 10 ml of saline appears very similar. Upon subtraction of the saline IR spectrum from the glucose plus saline IR spectrum (for 100 mg of glucose), the results in FIG. 4 (for a limited portion of the IR spectrum) are obtained. These results in FIG. 4 show a pronounced peak for the glucose at a wavelength of $9.634\mu$. This shows a relative enhancement of certain infrared spectral features for glucose in this spectral region, specifically, a primary absorption peak at a wave length of $9.634\mu$, that is one absorption peak that is necessary for detection purposes. This particular range of the glucose spectrum is rich in spectral absorption peaks (specifically 5), which is a distinctive fingerprint for the substance used for the purpose of detection. This provides more pattern information for the glucose fingerprint, giving rise to a higher probability of detection. The use of this range is also advantageous as it lies between two absorption bands of water.

Figure 5:
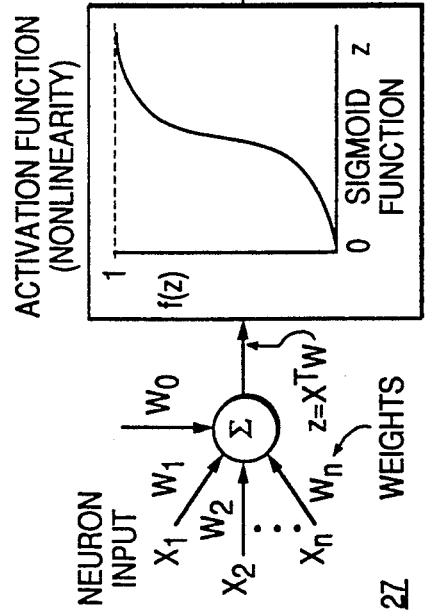
FIG. 5 illustrates a typical artificial neural network processing element.

The information shown in FIG. 4 is used to train the artificial neural network 26. The artificial neural network 26 comprises a plurality of simple processing elements 27, such as that shown in FIG. 5. The activation function (or squashing function) is a non-linearity as illustrated in FIG. 5.

Figure 6:
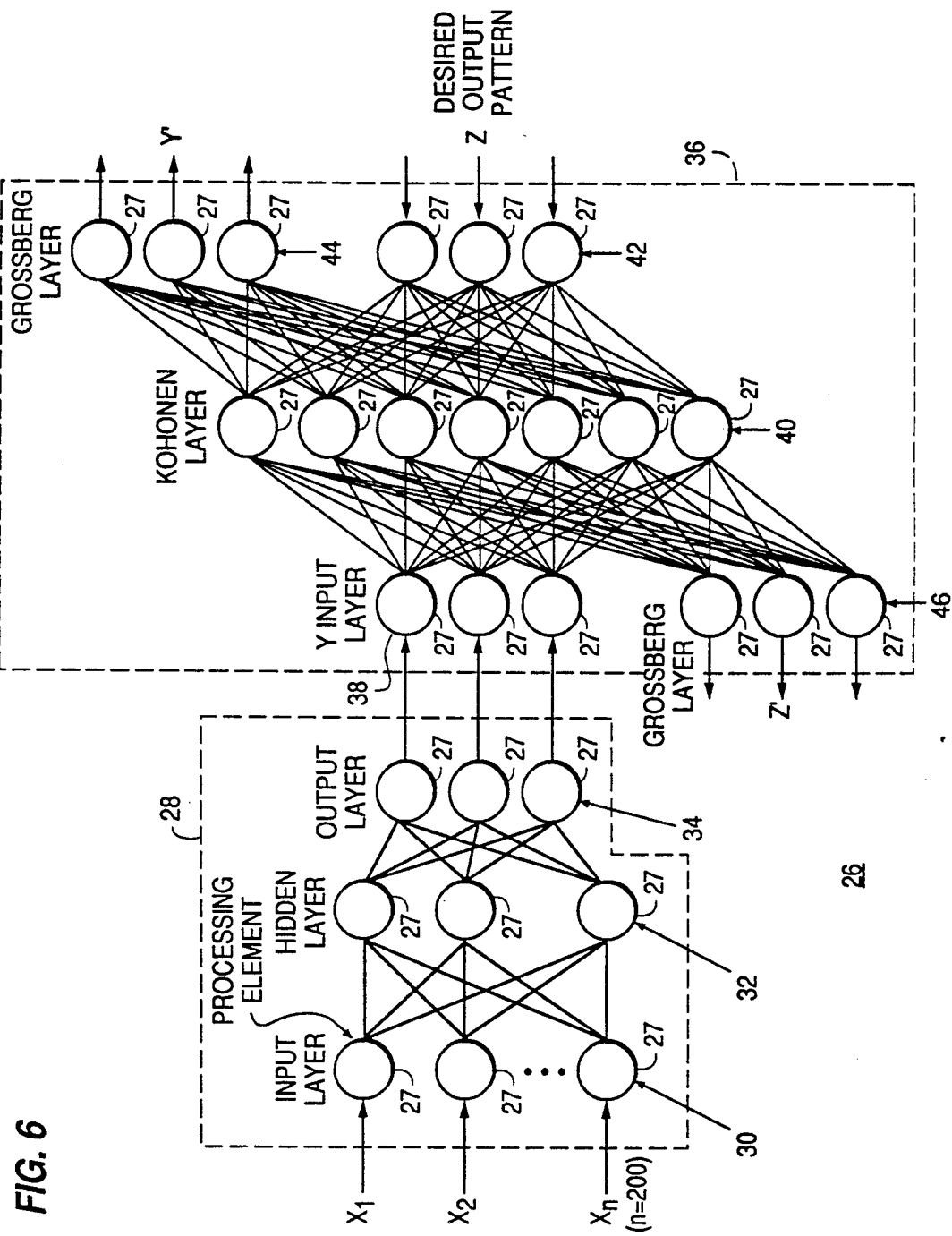
FIG. 6 illustrates an artificial neural network constructed in accordance with an embodiment of the present invention.

The artificial neural network detector 26, which detects the IR absorption characteristics of the particular condition that is of interest, is a hybrid artificial neural network and is illustrated in more detail in FIG. 6. The artificial neural network 26 comprises two known components that have hitherto not been combined in a single artificial neural network. The first component is the feedforward perceptron 28. The output of the feedforward perceptron 28 is coupled to another known component, a counterpropagation network 36.

The feedforward perceptron 28 receives an input pattern at an input layer 30, this input pattern consisting of normalized IR spectral samples. Each of the circles 27 in FIG. 6 represents a processing element 27 such as that shown in FIG. 5. The circled processing elements in the counterpropagation network 36 are linear elements with no activating function.

The processing elements 27 of the input layer are coupled to the processing elements 27 of a hidden layer 32. The processing elements 27 of the hidden layer 32 are coupled as shown to the processing elements of the output layer 34. The output of the feedforward perceptron 28 is provided as the input to the counterpropagation network 36.

The feedforward perceptron 28 is trained by a technique known as backpropagation in which an input is provided to the input layer 30 and the desired output for that input is also provided to the feedforward perceptron 28. Patterns are repeatedly presented to the feedforward perceptron 28 which is thereby trained to identify the patterns.

A feedforward perceptron 28 has very good noise rejection capabilities, but is somewhat deficient in performance relative to threshold decision settings. This problem is overcome in the present invention by using the counterpropagation network 36 in combination with the feedforward perceptron 28. The counterpropagation network 36 has relatively poor noise rejection capabilities in comparison to the feedforward perceptron 28, but is performance invariant relative to threshold decision settings.

The counterpropagation network 36 comprises a Y input layer 38 coupled to the output layer 34 of the feedforward perceptron 28. This Y input layer 38 is coupled to a Kohonen layer 40. The Kohonen layer 40 is a self-organizing layer that performs a competition between neurons, and whichever neuron "wins", this neuron fires to the output.

The Kohonen layer 40 is also coupled to another input layer 42 in which the desired output pattern Z (mentioned earlier) is provided as an input. Also coupled to the Kohonen layer are two output layers, the Grossberg layer 44 for output Y', and the Grossberg layer 46 for output Z'. The output of the Grossberg layer 46 for Z' represents the output of the artificial neural network detector 26. The output Y' of Grossberg layer 44 represents a replica of the output of the input to the counterpropagation network 36.

Using the hybrid artificial neural network 26 illustrated in FIG. 6, a very robust detection is provided. This is because the feedforward perceptron 28 provides an effective filtering of the noise produced by the measuring instrument and electronics, and the counterpropagation network 36 provides an architecture that is performance invariant relative to threshold decision settings to determine the glucose spectrum in blood that would be otherwise concealed by overlapping spectra from water and organic molecules, as well as by interfering reflectances from cells, platelets, etc. in blood.

Although the invention has been described for illustration purposes with respect to the detection of glucose in blood, the hybrid artificial neural network detector 26 of the present invention is useful in any number of settings in which a signal of interest may be concealed in a signal having noise and in which performance invariance relative to threshold decision settings is desirable. With proper training of the feedforward perceptron 28, as well as the use of an appropriate sensor, the artificial neural network detector 26 of the present invention could be used to detect other biological substances in blood and other body fluids, or to detect other conditions which can be represented by electrical signals.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. A method of filtering and classifying a signal of interest from background noise, comprising:
   receiving in an artificial neural network a digital signal containing a signal of interest and background noise;
   filtering out the background noise to produce a filtered signal from the digital signal in a feedforward perceptron of the artificial neural network; and
   classifying the signal of interest from the filtered signal in a counterpropagation network of the artificial neural network.

2. The method of claim 1, wherein the counterpropagation network is performance invariant to threshold decision settings.

3. The method of claim 1, wherein the signal of interest is representative of a biological condition.

4. The method of claim 3, wherein the biological condition is glucose concentration in blood.

5. The method of claim 1, wherein the feedforward perceptron is a feedforward perceptron trained by backpropagation.

6. A method of sensing and classifying a condition of interest in a system from background noise, comprising:
sensing a parameter representative of the condition of interest and producing an electrical signal representative of the sensed parameter;
converting the electrical signal into a digital signal, said digital signal containing a signal of interest representative of the condition of interest and background noise;
receiving in an artificial neural network the digital signal containing the signal of interest and the background noise;
filtering out the background noise in the artificial neural network to produce a filtered signal from the digital signal; and
classifying the signal of interest from the filtered signal in the artificial neural network to produce an output representative of the classified signal.

7. The method of claim 6, wherein the step of sensing includes performing infrared absorption and evanescent field spectroscopy.

8. The method of claim 6, wherein the step of filtering is performed by a feedforward perceptron.

9. The method of claim 8 wherein the step of classifying is performed by a counterpropagation network.

10. A device for filtering and classifying a signal of interest from background noise, comprising:
means for receiving in an artificial neural network a digital signal containing a signal of interest and background noise;
means for filtering out the background noise from the digital signal to produce a filtered signal; and
means for classifying the signal of interest from the filtered signal.

11. The device of claim 10, wherein the means for filtering is a feedforward perceptron.

12. The device of claim 11, wherein the means for classifying is a counterpropagation network.

13. The device of claim 10, wherein the means for classifying is a counterpropagation network.

14. A device for sensing and classifying a condition of interest in a system from background noise, comprising:
means for sensing a parameter representative of the condition of interest and producing an electrical signal representative of the sensed parameter;
means for converting the electrical signal into a digital signal, said digital signal containing a signal of interest representative of the condition of interest and background noise;
means for receiving in an artificial neural network the digital signal containing the signal of interest and the background noise;
means for filtering out the background noise in the artificial neural network to produce a filtered signal from the digital signal; and
means for classifying the signal of interest from the filtered signal in the artificial neural network to produce an output representative of the classified signal.

15. The device of claim 14, wherein the means for filtering is a feedforward perceptron.

16. The device of claim 15, wherein the means for classifying is a counterpropagation network.

17. The device of claim 14, wherein the means for classifying is a counterpropagation network.

18. A device for measuring a condition of a biological system, comprising:
a sensor that senses a parameter representative of the condition of interest in the biological system, said sensor producing a signal representative of the sensed parameter and containing background noise;
a converter coupled to the sensor to convert the signal produced by the sensor to a digital signal, said digital signal containing a signal of interest and background noise; and
an artificial neural network coupled to the converter, said artificial neural network filtering the background noise from the digital signal to produce a filtered signal and classifying the signal of interest from the filtered signal in the artificial neural network to produce an output representative of the classified signal.

19. The device of claim 18, wherein the sensor includes means for performing infrared absorption and evanescent field spectroscopy.

20. The device of claim 19, wherein the sensor includes an infrared waveguide, an infrared source, and a detector, said infrared source acting on the biological system and providing an infrared signal via said infrared waveguide to the detector, said detector converting said infrared signal into an electronic signal.

21. The device of claim 20, wherein the artificial neural network includes a feedforward perceptron coupled to the converter and which performs the filtering by the artificial neural network, and a counterpropagation network coupled to the feedforward perceptron and which performs the classifying by the artificial neural network.

22. The device of claim 21, wherein the condition of the biological system to be measured is concentration of specific types of molecules in a fluid.

23. The device of claim 21, wherein the condition of the biological system to be measured is concentration of glucose in blood.

24. The device of claim 23, wherein the device is implantable in vivo.

25. The device of claim 18, wherein the device is implantable in vivo.

* * * * *